United States Patent [19]

Assouly

[11] 4,135,510

[45] Jan. 23, 1979

[54] SYRINGE BARREL

[75] Inventor: Pierre Assouly, Puteaux, France

[73] Assignee: Schering Corporation, Kenilworth, N.J.

[21] Appl. No.: 789,040

[22] Filed: Apr. 20, 1977

[30] Foreign Application Priority Data

Feb. 9, 1977 [FR] France .................. 77 03638

[51] Int. Cl.² ............................................. A61M 5/00
[52] U.S. Cl. ................................. 128/218 R; 128/234
[58] Field of Search ............... 128/218 R, 218 C, 234, 128/215, 220, 221

[56] References Cited

U.S. PATENT DOCUMENTS

| 2,585,815 | 2/1952 | McLintock | 128/218 C |
| 3,216,616 | 11/1965 | Blankenship, Jr. | 128/218 C X |
| 3,353,718 | 11/1967 | McLay | 128/218 C X |
| 3,417,904 | 12/1968 | McLay | 128/218 C X |
| 3,677,448 | 7/1972 | Harris, Sr. et al. | 128/218 C X |

Primary Examiner—John D. Yasko
Attorney, Agent, or Firm—Vincent H. Gifford; Bruce M. Eisen

[57] ABSTRACT

A syringe barrel particularly advantageous for a disposable tip cap syringe which contains a prefilled suspension. The central bore of the syringe barrel has a diameter of 0.3 to 0.7 mm and thereby minimizes the settling of a suspended medicament within the syringe bore.

10 Claims, 4 Drawing Figures

SYRINGE BARREL

This invention relates to an improvement in syringe barrels, particularly a disposable syringe intended to be prefilled with a medicament suspension. It minimizes the loss of suspended material during the handling of the syringe thereby insuring that the patient will receive both the correct dosage and a uniform concentration of the medicament during injection.

Conventional syringes normally comprise a tubular body serving as a container for the medicament, a plunger slideably arranged within the tubular body, and a needle holding tip (hub). The needle holding tip has a central bore and is adapted to hold a standard needle. The needle is either permanently attached to the needle tip as shown in U.S. Pat. No. 3,216,616, or individually mounted just prior to use as shown in U.S. Pat. No. 3,161,195.

A common variety of prefilled syringe is known as a tip cap syringe (e.g., U.S. Pat. No. 3,161,195). This variety of syringe, which is usually disposed of after a single use, derives its name from the characteristic shield (cap) which protects and seals the end of the needle holding tip. A common feature of many tip shields is the integral protuberance which is adapted to extend into the bore of the needle holding tip to provide a better seal. The tip cap syringe has gained wide acceptance because it allows the physician to select the needle size. It also minimizes the possibility of needle damage during shipping.

It is not uncommon for a prefilled syringe to be placed in storage for a considerable period of time. In the case of a medicament suspension, this results in the suspension material being deposited in a cake. The physician or other user resuspends the caked material by vigorously shaking the contents just prior to use. Unfortunately, if the syringe has been stored for even a relatively short period of time with the needle tip facing down, a considerable portion of the suspended material will be deposited within the bore of the needle holding tip, and agitation may not dislodge this material from the bore. A further disadvantage may occur after the caked material is resuspended, since the particles sometimes aggregate or flocculate into a larger mass which results in a non-uniform suspension.

If the bore of the needle holding tip becomes clogged with a plug of active ingredient it is quite likely that a significant portion of the active material will be lost when the syringe is prepared for use. This loss can occur via a suction effect when the tip is removed, particularly those tips having protuberances, or in purging air from the syringe body or needle prior to injection of the medicament. The loss may represent a significant portion of the active material and will result in the patient receiving a smaller dose than was intended. Overall losses of 10–20% of the total active material are not uncommon.

If all of the active material in the bore is not lost during the purging operation, then the patient will very likely initially receive this aggregated plug of the suspended material instead of a uniform injection of small discrete particles as was intended. This could possibly result in the active ingredient being released to the patient's system in a different manner than was intended.

It has also been found that the particle distribution after resuspension of the caked material may differ from the distribution that was first intended due to the tendency of the particles to physically interlace (aggregate) or electrostatically attract (flocculate) into a larger mass.

It is an object of the present invention to provide a syringe barrel which obviates or reduces the aforementioned disadvantages.

It has surprisingly been found that when the novel syringe barrel is used in combination with a medicament suspension, the actual amount of particulate matter deposited in the tip is far less than would be expected from the actual reduction in the nozzle volume. It has also been found that during the injection the reduced bore will aid in separating any aggregated or flocculated particles.

According to the present invention, there is provided a barrel for a syringe comprising a tubular body having a first open end which is adapted to sealingly receive a syringe plunger, and a tip end with a central bore or passage. The central bore comprises a capillary portion with a diameter of 0.3 to 0.7 mm and a flared distal portion with a diameter greater than said capillary portion. If the barrel is to be used in a tip cap syringe, the outer surface of the tip end would be tapered. This taper provides a better seal for both the tip shield and the needle which is attached after the removal of the shield. It also permits the tip shield to be inserted over the tip end without damage. The tapered surface of the tip end also allows for greater selectivity in choosing a needle since a tapered surface provides flexibility in the needle collar tolerance.

Figure 1:
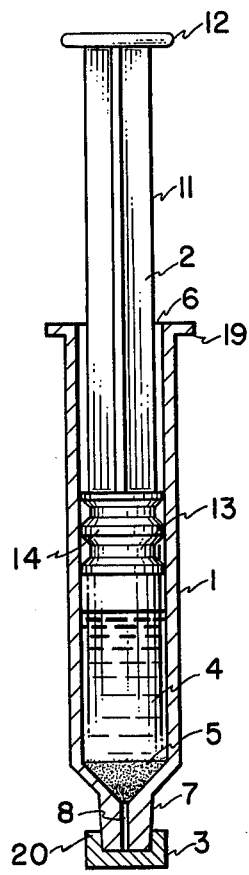
FIG. 1 is a sectional view of a prefilled tip cap syringe employing the novel bore tip.

FIG. 1 shows a prefilled tip cap syringe assembly comprising a barrel 1, a plunger 2 and a tip shield 3. The barrel is preferably made of glass. The syringe is shown prefilled with a suspension 4, a portion of which has settled into a cake 5 at the bottom of the syringe barrel. The barrel further comprises a first open end 6 which is adapted to receive the plunger, and a tip end 7 which is tapered at its outer surface. The tapered surface is adapted to releasably receive the collar 20 of the tip shield and to securely hold the syringe needle (FIG. 2) after the tip shield is removed. The central bore of the tip end has a capillary portion 8 which has a diameter of 0.3–0.7 mm. The plunger comprises an actuating rod portion 11 having a handle 12 at one end and a resilient tip 13 at the other end. The plunger tip has annular rings 14 which provide a better seal with the barrel and permit a greater degree of tolerance toward variations in the internal diameter of the barrel. The tip is preferably made of a surgical grade of silicone rubber. At the first open end 6 is a flange 19 acting in a conventional manner as a finger hold for the syringe. The rod portion 11 is preferably cruciform in cross section and constructed of polystyrene.

Figure 2:
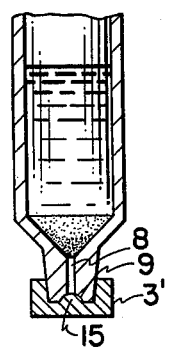
FIG. 2 is a partial sectional view of a needle holding tip in combination with a preferred tip cap shield having an integral protuberance.

FIG. 2 shows a preferred reduced bore tip having a flared distal portion 9. The preferred tip shield 3' in this embodiment contains an integral protuberance which protrudes into the flared distal or terminal portion 9 of the syringe bore to provide a better seal at the tip end. The tip shield is preferably made of a surgical grade of silicone rubber. Ideally the protuberance mates in a fluid-tight fit with the flared distal portion, as shown in FIG. 2. In practice, however, the protuberance only extends part way into the flared distal portion, thereby simplifying the assembly of the two components.

Figure 3:
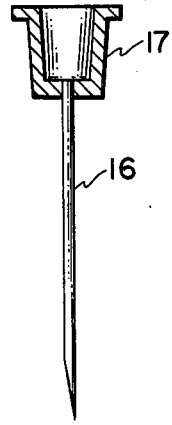
FIG. 3 is a needle which is adapted to mate with the tip cap syringe of FIGS. 1 or 2.

FIG. 3 shows a needle 16 which is adapted to mate over the tip end of the syringe barrel. The inside surface of the needle collar 17 is tapered to mate with the outer surface of the tapered tip end.

Figure 4:
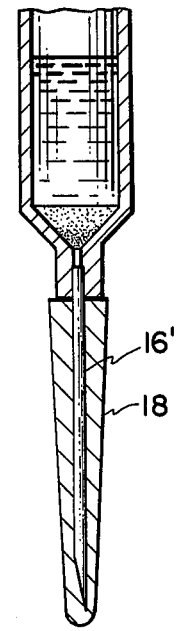
FIG. 4 is a partial sectional view of a tip with a preattached needle.

FIG. 4 shows the reduced bore syringe barrel tip with the needle 16' integrally attached to the needle tip end by a suitable adhesive or other means. The tip of the syringe is sealed via a removable needle guard 18.

The capillary portion 8 preferably has an internal diameter of from 0.4–0.6 mm, most preferably of substantially 0.5 mm. The overall length of the passageway is preferably 7 to 15 mm.

In the FIG. 2 preferred embodiment the ratio of the length of the capillary portion 8 to the overall length of the bore generally lies between 0.2:1 and 0.8:1, preferably between 0.6:1 and 0.8:1. The internal diameter of the distal portion 9 is preferably of circular cross section and having a diameter of from greater than 1.0 mm to 2.0 mm.

The advantage obtainable with a syringe barrel constructed in accordance with the invention over a syringe of prior art construction may be illustrated by the following comparison test.

A prior art syringe was prefilled with 1.0 ml of an aqueous suspension containing 6.4 mg of betamethasone dipropionate having a particle size of 20 microns or less and a bulk density of 88 mg/ml. The syringe tip has a uniform axial passageway which was 10 mm in length and 1.15 mm in diameter. A stopper with a protuberance, such as 3', having a height of 1.5 mm was used to seal the tip end. The syringe was stored with the nozzle piece downward for one week, such time resulting in essentially complete sedimentation of the suspended particles.

A syringe employing a reduced bore barrel was similarly filled and stored with the identical suspension of betamethasone dipropionate as used for the prior art storage. The novel syringe had a capillary portion of 7.0 mm length and 0.5 mm diameter and a distal flared portion of 3.0 mm length and 1.15 mm diameter. The stopper, which was identical to the one used for the prior art syringe, extended 1.5 mm into the passageway. The bore volume of the prior art syringe, which was essentially fully occupied by a suspended medicament, was about 3 times the bore volume in the reduced bore syringe.

The amount of active material which was deposited in each of the syringes was carefully measured. The amount of active material deposited in the prior art syringe, which could not be redispensed by shaking, was greater than 0.77 mg, or approximately 12% of the total amount of the active ingredient. The amount of active material deposited in the reduced bore syringe was only 0.019 mg. As is apparent, the amount deposited in the reduced bore syringe is far less than would be expected based on differences in calculated volumes between the two syringes.

The syringe barrel would be primarily utilized for premixed suspensions, particularly suspensions in which the majority of particles are less than 50 microns in size, preferably suspensions in which the majority of particles are less than 20 microns.

It is apparent, however, that the reduced bore syringe could also be utilized for solutions, or in a dual compartment syringe, such as in U.S. Pat. No. 3,756,390, if a parenteral manufacturer desired to standardize its entire syringe line.

The reduced bore syringe has numerous other advantages over the conventional syringes whether they be used for suspensions or solutions. For one, there is less material wasted during use of the reduced bore syringe since less material is retained in the bore after injection. Also, there is less likelihood of contamination from the rubber shield due to the smaller area at the medicament/rubber interface, thereby providing less of a likelihood or diffusion into or out of the rubber tip.

In a disposable syringe the reduced bore barrel has a further advantage in that it renders it difficult to refill the syringe from a vial of a medicament suspension. This helps to avoid the obvious danger in accidentally reusing a syringe which was intended for disposal after a single use.

The foregoing disclosure and description is illustrative and explanatory. Various other modifications will occur to those skilled in the art.

What is claimed is:

1. A prefilled syringe which minimizes the settling of a suspended medicament within the syringe bore comprising:
   a barrel;
   a plunger extending within said barrel;
   a needle holding tip with a bore, said bore comprising a capillary portion having a 0.3 to 0.7 mm diameter and a flared distal portion with a diameter greater than said capillary portion;
   a medicament suspension within said syringe;
   and a tip shield with an integral protrusion which extends into said flared distal end.

2. A syringe as in claim 1, wherein the majority of the suspension particles are less than 50 microns.

3. A syringe as in claim 1, wherein the diameter of said capillary portion is 0.4 to 0.6 mm.

4. A syringe as in claim 3, wherein said capillary diameter is substantially 0.5 mm.

5. A barrel for a tip cap syringe comprising:
   a tubular body having a first open end adapted to receive a syringe plunger; and
   a tip end having a central bore and a tapered outer surface, said central bore comprising a capillary portion with a 0.3 to 0.7 mm diameter, and a flared distal portion with a diameter greater than said capillary portion, said tapered outer surface of said tip end adapted to releasably receive a tip shield which protrudes into said flared distal portion and is further adapted to securely hold a syringe needle after the tip shield is removed.

6. A syringe assembly comprising:
   a barrel as in claim 5,
   a plunger extending within said barrel; and
   a tip shield releasably held by said tapered surface, said tip shield containing an integral protuberance extending within said flared distal portion.

7. A syringe as in claim 5, wherein the diameter of said capillary portion is 0.4 to 0.6 mm.

8. A syringe as in claim 5, wherein the ratio of the length of said capillary portion to the total length of said bore is from 0.2 to 0.8.

9. A syringe as in claim 8, wherein said ratio is from 0.6 to 0.8.

10. A syringe as in claim 5, wherein the diameter of said distal portion is greater than 1.0 mm.